United States Patent
Crea

(10) Patent No.: US 8,216,599 B2
(45) Date of Patent: Jul. 10, 2012

(54) METHOD FOR TREATMENT OF INFLAMMATION

(75) Inventor: Roberto Crea, San Mateo, CA (US)

(73) Assignee: CreAgri, Inc., Hayward, CA (US)

( * ) Notice: Subject to any disclaimer, the term of this patent is extended or adjusted under 35 U.S.C. 154(b) by 731 days.

(21) Appl. No.: 10/367,308

(22) Filed: Feb. 13, 2003

(65) Prior Publication Data

US 2004/0039066 A1 Feb. 26, 2004

Related U.S. Application Data

(60) Provisional application No. 60/356,847, filed on Feb. 13, 2002.

(51) Int. Cl.
*A61F 2/02* (2006.01)

(52) U.S. Cl. .................................................. 424/423

(58) Field of Classification Search .................. None
See application file for complete search history.

(56) References Cited

U.S. PATENT DOCUMENTS

| | | | |
|---|---|---|---|
| 4,370,274 A | 1/1983 | Finch et al. | |
| 4,452,744 A | 6/1984 | Finch et al. | |
| 4,522,119 A | 6/1985 | Finch et al. | |
| 5,059,431 A | 10/1991 | Daeschel et al. | |
| 5,714,150 A | 2/1998 | Nachman | |
| 5,719,129 A | 2/1998 | Andary et al. | |
| 5,998,641 A | 12/1999 | Ganguli et al. | |
| 6,117,844 A * | 9/2000 | Fredrickson | 514/27 |
| 6,162,480 A | 12/2000 | van Buuren et al. | |
| 6,165,475 A * | 12/2000 | Crea et al. | 424/769 |
| 6,197,308 B1 | 3/2001 | Crea et al. | |
| 6,358,542 B2 | 3/2002 | Cuomo et al. | |
| 6,361,803 B1 | 3/2002 | Cuomo et al. | |
| 6,416,808 B1 | 7/2002 | Crea | |
| 6,437,004 B1 | 8/2002 | Perricone | |
| 6,440,465 B1 | 8/2002 | Meisner | |
| 6,682,763 B2 | 1/2004 | Kuno et al. | |
| 6,746,706 B1 | 6/2004 | van der Boom et al. | |
| 6,849,770 B2 | 2/2005 | Guzman et al. | |
| 6,936,287 B1 | 8/2005 | Crea et al. | |
| 7,261,909 B2 | 8/2007 | Crea | |
| 2002/0004077 A1 | 1/2002 | Cuomo et al. | |
| 2002/0198415 A1 | 12/2002 | Crea | |
| 2003/0108651 A1 | 6/2003 | Crea | |
| 2003/0185921 A1 | 10/2003 | Fotinos et al. | |

(Continued)

FOREIGN PATENT DOCUMENTS

EP 0295722 12/1988

(Continued)

OTHER PUBLICATIONS

Saija et al, Olive Biophenols: Functional Effects on Human Wellbeing, Trends in Food Sciences & Technology, vol. 11, Issues 9-10, Sep. 10, 2000, p. 357-363.*

(Continued)

*Primary Examiner* — Carlos Azpuru
(74) *Attorney, Agent, or Firm* — Carr & Ferrell LLP

(57) ABSTRACT

A method of treating inflammation, an inflammatory condition, or AIDS-associated neurological disorder in a subject in need of such treatment is disclosed. The method includes administering to said subject a pharmaceutically effective amount of substantially purified hydroxytyrosol or a substantially purified mixture of hydroxytyrosol and oleuropein. Also disclosed are compositions for use in practicing the method.

16 Claims, 1 Drawing Sheet

U.S. PATENT DOCUMENTS

| | | |
|---|---|---|
| 2004/0039066 A1 | 2/2004 | Crea |
| 2005/0103711 A1 | 5/2005 | Emmons et al. |
| 2005/0158798 A1 | 7/2005 | Sher |
| 2006/0257351 A1 | 11/2006 | Chiba |
| 2007/0020350 A1 | 1/2007 | Numano et al. |
| 2007/0084797 A1 | 4/2007 | Cooper et al. |
| 2008/0026100 A1 | 1/2008 | Villa et al. |
| 2008/0090000 A1 | 4/2008 | Crea |

FOREIGN PATENT DOCUMENTS

| | | | |
|---|---|---|---|
| EP | 0581748 | | 7/1993 |
| EP | 0855908 | * | 8/1998 |
| EP | 1230926 A1 | | 8/2002 |
| ES | 2006904 | | 5/1989 |
| IT | 1276576 | | 11/1997 |
| IT | 1278025 | | 11/1997 |
| JP | 07-223940 A | | 8/1995 |
| JP | 08-119825 A | | 5/1996 |
| JP | 09-078061 A | | 3/1997 |
| JP | 2001-181197 A | | 7/2001 |
| JP | 2001-181632 A | | 7/2001 |
| JP | 2001-0348337 | | 12/2001 |
| WO | 97/28089 | | 8/1997 |
| WO | 97/39632 | | 10/1997 |
| WO | 97/47711 | | 12/1997 |
| WO | 00/36936 | | 6/2000 |
| WO | WO01/76579 A1 | | 10/2001 |
| WO | WO02/18310 A1 | | 3/2002 |
| WO | WO 03/032966 A1 | | 4/2003 |
| WO | 03/068171 | | 8/2003 |

OTHER PUBLICATIONS

Olive Leaf Extract, Pacific Health Sciences, 2006.*
Saija et al., *Intl. J. Pharm.*, 166:123-133, 1998.
Chimi et al., *JAOCS*, 68(5):307-312, 1991.
Fleming et al., *Applied Microbiology*, 18(5):856-860, 1969.
Manna et al., *Advances in Experimental Medicine and Biology*, 472:115-130 (1999).
Owen et al., *Lancet Oncology*, 1(2):107-112 (2000).
Adamson, D.C. et al., "Rate and severity of HIV-associated dementia (HAD): correlations with Gp41 and iNOS", *Mol. Med.* 5:98-109, 1999.
Addis, P.B. et al., "Atherogenic and anti-atherogenic factors in the human diet", *Biochem Soc Symp* 61:259-271, 1995.
Caruso, D. et al., "Effect of virgin olive oil phenolic compounds on in vitro oxidation of human low density lipoproteins", *Nutr. Metab. Cardiovasc. Dis.* 9(3):102-107, 1999.
Cohen, R.A. et al., "Neurocognitive performance enhanced by highly active antiretroviral therapy in HIV-infected women", *AIDS* 15:341-345, 2001.
Dal Pan, G.J. et al., "Chinicopathologic correlations of HIV-1-associated vacuolar myelopathy: an autopsy-based case-control study", *Neurology* 44:2159-2164, 1994.
Dore, G.J. et al., "Changes to AIDS dementia complex in the era of highly active antiretroviral therapy", *AIDS* 13:1249-1253, 1999.
Ellis, R.J. et al., "Cerebrospinal fluid human immunodeficiency virus type 1 RNA levels are elevated in neurocognitively impaired individuals with acquired immunodeficiency syndrome", *HIV Neurobehavioral Research Center Group in Ann. Neurol.* 42:679-688, 1997.
Enting, R.H. et al., "Cerebrospinal fluid beta2-microglobulin, monocyte chemotactic protein-1, and soluble tumor necrosis factor alpha receptors before and after treatment with Lamivudine plus zivovudine or stavudine", *J. Neuroimmunol* 102(2):216-221, 2000.
Glass J.D., et al ., "Microglia in HIV-associated neurological diseases", *Microscopy Research and Technique* 54:95-105, 2001.
Glass J.D. et al. "Immunocytochemical quantitation of HIV virus in the brain: correlations with dementia", *Ann Neurol* 38:755-762, 1995.
Lipton S.A. and Gendleman H.E., "Dementia associated with the acquired immunodeficiency syndrome", *N. Engl J Med* 332:934-940, 1995.
Koutsilieri E. et al., "Neurotransmission in HIV associated dementia: a short review", *J Neural Transm* 108:767-775, 2001.
Mazur A. et al., "Inhibitory effect of procyanidin-rich extracts on LDL oxidation in vitro", *Atherosclerosis* 145:421-422, 1999.
Masliah E. et al., "Changes in pathological findings at autopsy in AIDS cases for the last 15 years", *AIDS* 14:69-74, 2000.
McArthur J.C., "Neurologic manifestations of AIDS", *Medicine* 66:407-437, 1987.
McGuire D. and Marder K., "Pharmacologic frontiers in the treatment of AIDS dementia", *J Psychopharmacol* 14(3):251-257, 2000.
Ng T.B, et al., "Anti-Human Immunodeficiency Virus (Anti-HIV) Natural Products with Special Emphasis on HIV Reverse Transcriptase inhibitors", *Life Sci* 61(10):933-49, 1997.
Napoli C. and Lerman L.O., "Involvement of oxidation-sensitive mechanisms in the cardiovascular effects of hypercholesterolemia", *Mayo Clin Proc* 76:619-631, 2001.
Nottet H.S. and Gendelman H.E., "Unraveling the neuroimmune mechanisms for the HI4:281-290V-1-associated cognitive/motor complex", *Immunol Today* 16(9):441-448, 1995.
Petito C.K., et al., "Vacuolar myelopathy pathologically resembling subacute combined degeneration in patients with the acquired immunodeficiency syndrome", *N. Engl J Med* 312:874-879, 1985.
Practico D. et al., "Increased F2-isoprostanes in Alzheimer's disease: evidence for enhanced lipid peroxidation in vivo", *FASEB J* 12 (15):1777-1783, 1998.
Rice-Evans C., "Plant polyphenols: free radical scavengers or chain-breaking antioxidants?", *Biochem Soc Symp* 61:103-116, 1995.
Rimbach G. et al., "Methods to assess free radicals and oxidative stress in biological systems", *Arch Tieremahr* 52(3):203-222, 1999.
Ryan, L.A. et al., "Plasma Levels of Soluble CD14 and Tumor Necrosis Factor-alpha Type II Receptor Correlate with Cognitive Dysfunction during Human Immunodeficiency Virus Type 1 Infection:", *J Infect Dis* 184: 699-706, 2001.
Sarkkinen, E.S. et al., "Effects of two low-fat diets, high and low in polyunsaturated fatty acids, on plasma lipid peroxides and serum vitamin E levels in free-living hypercholesterolaemic men", *Eur J Clin Nut* 47:623-630, 1993.
Shi B, et al., "Neuronal apoptosis induced by HIV-1 tat protein and TNF alpha: potentiation of neurotoxicity mediated by oxidative stress and implications for AIDS dementia", *J Neurosci* 18(22):9326-34, 1998.
Treitinger A. et al., "Decreased antioxidant defense in individuals infected by the human immunodeficiency virus", *Eur J Clin Invest* 30(5):454-459, 2000.
Visioli F. et al., "Olive oils rich in natural catecholic phenols decrease isoprostane excretion in humans", *Biochem Biophys Res Commun* 278(3):797-799, 2000.
Visioli F. and Galli C., "Antiatherogenic components of olive oil", *Curr Atheroscler Rep* 3(1):64-67, 2001.
Le Tutour and Guedon, "Antioxidant activities of Olea europaea leaves and related phenolic compounds", Phytochemistry, vol. 31, No. 4, pp. 1173-1178 (1992) doi:10.1016/0031-9422(92)80255-D Abstract only.
Ragione et al., "Hydroxytyrosol, a natural molecule occurring in olive oil, induces cytochrome c-dependent apoptosis", Biochem. Biophys. Res. Commun., vol. 278, No. 3, pp. 733-739 (2000).
Visioli, "'Waste waters' from olive oil production are rich in natural antioxidants", Experientia, vol. 51, No. 1, pp. P32-P34, (1995) Abstract Only.
Visioli et al., "Antioxidant and other biological activities of olive mill waste waters", J. Agric. Food. Chem., vol. 47, No. 8, pp. 3397-3401 (1999).
Visioli et al., "Olive phenol hydroxytyrosol prevents passive smoking-induced oxidative stress", Circulation, vol. 102, No. 18, pp. 2169-2171 (2000).
Walter et al., "Preparation of antimicrobial compounds by hydrolysis of oleuropein from green olives", Appl. Microbiol., vol. 26, No. 5, pp. 773-776 (1973).
Amalfitano, G., Commission of the European Communities, Luxemborg, 145-150 OSTI of DE910018386 Conference: Energy Innovation and the Agro-Food Industry (Abstract) (1990).
Amari, S. et al., "Olive Leaves: Their Extract Performs Effective Antiradicalic Action", SOFW Journal, vol. 125, No. 8, 30-32 (1999).

Armstrong, B.K., et al. "Environmental Factors and Cancer Incidence and Mortality in Different Countries, with Special Reference to Dietary Practices", International Journal of Cancer, 15:617-631 (1975).

Aziz et al., "Comparative Antibacterial and Antifungal Effects of Some Phenolic Compounds", Microbios, 93: 43-54 (1998).

Bartsch, H. et al., "Dietary Polyunsaturated Fatty Acids and Cancers of the Breast and Colorectum: Emerging Evidence for Their Role as Risk Modifiers", Carcinogenesis, 20(12): 2209-2218 (1999).

Bonina, F. et al., "Biofenoli Dell'ulivo", Cosm. Technol. (No English translation available), 2131: 18-22 (1999).

Braga et al., "Olive Oil, Other Seasoning Fats, and the Risk of Colorectal Carcinoma", American Cancer Society, 82: 448-453 (1998).

Bruner et al., "A Systematic Review of Adverse Effects Associated with Topical Treatments for Psoriasis", Dermatology Oline Journal, 9(1):2, 11 pages. (2003).

Capasso et al., "A Highly Convenient Synthesis of Hyrdoxytyrosol and its Recovery from Agricultural Waste Waters", J. Agric. Food Chem., 47(4) 1745-1748 (1999).

Capasso et al., "Isolation Spectroscopy and Selective Phytotoxic Effects of Polyphenols from Vegetable Waste Waters", Phytochemistry, 31(12): 4125-4128 (1992).

Chan et al. "What Causes Prostate Cancer? A Brief Summary of Epidemiology", Seminars in Cancer Biology, 8: 263-273 (1998).

D'Amicis, A. et al., "Olive Oil Consumption and Cancer Mortality in Italy", Advances in Nutrition and Cancer 2 (67-72, Kluwer Academic/Plenum Publishers, New York (1999).

De La Puerta et al., "Inhibition of Leukocyte 5-Lipoxygenase by Phenolics from Virgin Olive Oil", Biochemical Pharmacology, 57: 445-449 (1999).

Deiana et al., "Inhibition of Peroxynitrite Dependent DNA Base Modification and Tyrosine Nitration by the Extra Virgin Olive Oil-Derived Antioxidant Hydroxytyrosol", Free Radical Biology and Medicine, 26: 762-769 (1999).

Fehri, B. et al., "Olea Europaea L.: Stimulan, Anti-Ulcer and Anti-Inflammatory Effects", Boll. Chim. Farmaceutico, vol. 135, No. , 43-49 (1996).

Feletar et al., "Treatment of Refractory Psoriatic Arthritis with Infliximab: a 12 Month Observational Study of 16 Patients", Ann. Rheum Dis., 63: 156-161 (2004).

Ficarra et al., "HPLC Analysis of Oleuropein and Some Flavonoids in Leaf and Bud of Olea Europaea L.", IL Farmaco, 46(6): 803-815 (1991).

Gerber et al., Epidemiology of Diet and Cancer, Olive Oil and Cancer, Chapter 13, pp. 263-275, edited by M.J. Jill, Ellis Horwood, New York (1994).

Ho, V.C., "The Use of Ciclosporin in Psoriasis: A Clinical Review", Br. J. Dermatology, 150(Suppl. 67) 1-10 (2004).

Kiritsakis, A.K., "Flavor Components of Olive Oil—A Review", Journal of American Oil Chemists' Society, vol. 75, 673-681 (1998).

Kobayashi et al., "An Alternative to Atopic Dermatitis: Part 1" Case Series Presentation eCAM, 1(1) 49-62 (2004).

Kohyama et al., "Inhibition of Arachidonate Lopoxygenase Activities by 2-(3,4-Dihyrdoxyphenol)ethanol, a Phenolic Compound from Olives", Biosci. Biotech. Biochem., 61(2): 347-350 (1997).

Koutsoumanis et al., "Modeling the Effectiveness of a Natural Antimicrobial on Salmonella enteritidis as a Function of Concentration, Temperature and pH, Using Conductance Measurements", Journal of Applied Microbiology, 84: 981-987 (1998).

Kuller et al., "Dietary Fat and Chronic Diseases: Epidemiologic Overview", Journal of the America Dietetic Association, 97:S9-S15 (1997).

La Vecchia et al., "Monounsaturated and Other Types of Fat, and the Risk of Breast Cancer", European Journal of Cancer Prevention, 7: 461-464 (1998).

Lebwohl et al., "Psoriasis Treatment: Traditional Therapy", Ann. Rheum Dis., 64(Suppl. 2): ii83-ii86 (2005)/.

Limiroli et al., "1H NMR Study of Phenoloics in Vegetation Water of Three Cultivars of Olea Europaea: Similarities and Differences", Journal of Agricultural and Food Chemistry, 44(8): 2040-2048 (Abstract) (1996).

Manna et al., "Transport Mechanism and Metabolism of Olive Oil Hydroxytyrosol in CAco-2 Cells", FEBS Letters, 470: 341-344 (2000).

Marchetti et al., "Treatments for Mild-To-Moderate Recalcitrant Plaque Psoriasis: Expected Clinical and Economic Outcomes for First-Line and Second-Line Care", Dermatology Online Journal, 11(1) 11 pages. (2005).

Martin-Moreno et al., "Dietary Fat, Olive Oil Intake and Breast Cancer Risk", Int. J. Cancer, 58: 774-780 (1994).

Mason and Krueger, "Thioguanine for Refractory Psoriasis: A 4-Year Experience", J. Am. Acad. Dermatol., 44(6) 67-72 (2001).

Mattson, F.H. et al., "Comparison and Effects of Dietary Saturated, Mono-unsaturated, and Poly-unsaturated Fatty Acid on Plasma Lipids and Lipoproteins in Man", J. Lipid Res., 26: 194-202 (1985).

Owen, R.W. et al. "The Antioxidant/Anticancer Potential of Phenolic Compounds Isolated from Olive Oil", European Journal of Cancer, 36: 1235-1247 (2000).

Owen, R.W. et al., "Phenolic Compounds and Squalene in Olive Oils: The Concentration and Antioxidant Potential of Total Phenols, Simple Phenols, Secoiridoids, Lignans and Squalene", Food Chemical Toxicology, 38: 647-659 (2000).

Owen, R.W. et al., "The Identification of Lignans as Major Components of the Phenolic Fraction of Olive Oil", J. Can. Res. Clin. Onc., 125:S31 (Abstract K22) (2000).

Papadopoulos, G. et al., "Antioxidant Effect of Natural Phenols on Olive Oil", Journal of the American Oil Chemists' Society, vol. 68, No. 9, 669-671 (1991).

Papadopoulos, G. et al., "Stability of Virgin Olive Oil: Assessment of Natural Antioxidants and Other Related Factors", Food Flavours, Ingredients and Composition, G., Ed., Elsevier, Amsterdam, 321-326 (1993).

Parthasarathy, S. et al., "Low Density Lipoprotein Rich in Oleic Acid is Protected Against Oxidative Modification: Implications for Dietary Prevention of Atherosclerosis", Proc. Natl. Acad. Sci. USA, 87: 3894-3898 (1990).

Petroni, a. et al., "Inhibition of Platelet Aggregation and Eicosanoid Production by Phenolic Components of Olive Oil", Thrombosis Research, 78(2): 151-160 (1995).

Rifai et al., "Inflammatory Markers and Coronary Heart Disease", Curr. Opin. Lipidol., 13: 383-389 (2002).

Risch, H.A. et al., "Dietary Fat Intake and Risk of Epithelial Ovarian Cancer", Journal of the National Cancer Institute, 86: 1409-1415 (1994).

Roenigk, et al., Psoriasis, 2nd Edition, New York Marcel Dekker, 213-214 (1991).

First Report on Patent Application from the AU Patent Application No. 2003211118 dated Feb. 21, 2007 based on PCT/US2003/004761.

First Report on Patent Application from the AU Patent Application No. 2008249142 dated Jan. 29, 2010 based on PCT/US2003/004761.

Notice of Final Rejection from the JP Patent Application No. 2004-519909 dated Sep. 20, 2011 based on PCT/US2003/021111.

Request for Amendment from the AU Patent Application No. 2003211118 dated Septemeber 22, 2008 based on PCT/US2003/004761.

Request for Amendment from the AU Patent Application No. 2008249142 dated Oct. 21, 2011 based on PCT/US2003/004761.

Response to Offical Action from the CA Patent Application No. 2474798 dated May 3, 2010 based on PCT/US2006/004761.

Response to Official Action dated Feb. 16, 2010 for the AU Patent Application No. 2003249719 based on PCT/US2003/021111.

Response to Official Communication from the EP Patent Application No. 03739832.8 dated Nov. 30, 2010 based on PCT/US2006/004761.

Response to the Official Action for the EP Patent Application No. 03763237.9 dated Feb. 9, 2010 based on PCT/US2003/021111.

Response to the EP Patent Office from the EP Patent Application No. 06788032.8 dated Feb. 1, 2010 based on PCT/US2006/028265.

Second Report on Patent Application from the AU Patent Application No. 2003211118 dated Sep. 30, 2008 based on PCT/US2003/004761.

Amendment to the EP Patent Office from the EP Patent Application No. 06788032.8 dated Mar. 1, 2011 based on PCT/US2006/028265.

Offical Action from the AU Patent Application No. 2006269843 dated Mar. 11, 2011 based on PCT/US2006/028265.

Official Action dated Jun. 26, 2008 from the AU Patent Application No. 2003249719 based on PCT/US2003/021111.
Official Action dated Oct. 28, 2009 from the JP Patent Application No. 2004-519909 based on PCT/US2003/021111.
Official Action from the CA Patent Application No. 2491613 dated Jul. 20, 2010 based on PCT/US2003/021111.
Official Action from the EP Patent Application No. 03763237.9 dated Jul. 30, 2009 based on PCT/US2003/021111.
Official Action from the JP Patent Application No. 2004-519909 dated Jun. 30, 2010 based on PCT/US2003/021111.
Official Action from the JP Patent Application No. 2004-519909 dated Oct. 26, 2009 based on PCT/US2003/021111.
Official Action from the KR Patent Application No. Oct. 2005-7000208 dated Nov. 24, 2009 based on PCT/US2003/021111.
Official Communication from the CA Patent Application No. 2474798 dated Nov. 3, 2009 based on PCT/US2006/004761.
Official Communication from the EP Patent Application No. 03739832.8 dated Feb. 1, 2012 based on PCT/US2006/004761.
Official Communication from the EP Patent Application No. 03739832.8 dated Feb. 12, 2010 based on PCT/US2006/004761.
Official Communication from the EP Patent Application No. 06788032.8 dated Dec. 7, 2009 based on PCT/US2006/028265.
Official Communication from the EP Patent Application No. 06788032.8 dated Sep. 27, 2011 based on PCT/US2006/028265.
Official Communication from the IN Patent Application No. 308/MUMNP/2008 dated Sep. 21, 2011 based on PCT/US2006/028265.
Examination Report from the NZ Patent Application No. 534884 dated Jan. 17, 2007 based on PCT/US2006/004761.
Examination Report from the NZ Patent Application No. 534884 dated Nov. 22, 2005 based on PCT/US2006/004761.
Notice of Final Rejection from the JP Patent Application No. 2003-567356.4 dated Jun. 15, 2010 based on PCT/US2006/004761.
Notice of Grounds for Rejection from the KR Patent Application No. 10-2004-7012613 dated Nov. 20, 2009 based on PCT/US2006/004761.
Notice of Reasons for Rejection from the JP Patent Application No. 2003-567356.4 dated May 22, 2009 based on PCT/US2006/004761.
Notification of Rejection from the CN Patent Application No. 03803885.4 dated Aug. 1, 2008 based on PCT/US2006/004761.
Response to Examination Report from the NZ Patent Application No. 534884 dated Dec. 15, 2006 based on PCT/US2006/004761.
Response to Examination Report from the NZ Patent Application No. 534884 dated Mar. 15, 2007 based on PCT/US2006/004761.
Romani, a. et al., "Polyphenolic Content in Five Tuscany Cultivars of Olea Europaea L." J. Agric. Food Chem., 47: 964-967 (1999).
Rutledge, "Anti-Inflammatories", Dermatology Times, 24(10), pp. 1-4 of Proquest (2003).
Servili et al., "High-Performance Liquid Chromatography Evaluation of Phenols in Olive Fruit, Virgin Olive Oil, Vegetation Waters and Pomace and 1D- and 2D- Nuclear Magnetic Resonance Characterization", Journal of the Americal Oil Chemists' Society, 76(7): 873-882 (Abstract) (1999).
Tassou et al., "Inhibition of Salmonella Enteritidis by Oleuropein in Broth and in a Model Food System", Letters in Applied Microbiology, 20(2): 120-124 (1995).
Tranter et al., "The Effect of the Olive Phenolic Compound, Oleuropein, on Growth and Enterotoxin B Production by Staphylococcus Aureus", Journal of Applied Bacteriology, 74(3) 253-259 (1993).
Tsimidou, M. et al., "Determination of Phenolic Compounds in Virgin Olive Oil by reversed-Phase HPLC and Emphasis on UV Detection", Food Chemistry, 44: 53-60 (1992).
Tsimidou, M. et al., "Phenolic Compounds and Stability of Virgin Olive Oil—Part I", Food Chemistry, vol. 45, 141-144 (1991).
Tuck, et al. "Major Phenolic Compounds in Olive: Metabolism and Health Effects", Journal of Nutritional Biochemistry, 13: 636-644 (2002).
umm.edu. Herbal Medicine. Retrieved from the internet on Jan. 30, 2011 <http://www.umm.edu/altmed/articles/herbal-medicine-000351.htm>. 9 pages.
Visioli et al., "Olive Oil Phenolics are Dose-dependently Absorbed in Humans", FEBS Letters, 468(2): 159-160 (2000).
Visioli et al., "The effect of minor constituents of olive oil on cardiovascular disease: new findings", Nutr. Rev., 56: 142-147 (abstract only) (1998).
Visioli, F. et al., "Free Radical-Scavenging Properties of Olive Oil Polyphenols", Biochemical and Biophysical Research Communications, vol. 247, No. 1, 60-64 (1998).
Visoli et al., "Oleuropein, the Bitter Principle of Olives, Enhances Nitic Oxide Production by Mouse Macrophages", Life Sciences, 62(6): 541-546 (1998).

* cited by examiner

METHOD FOR TREATMENT OF INFLAMMATION

This application claims the priority benefit of U.S. Provisional Application No. 60/356,847, filed Feb. 13, 2002, which is incorporated herein in its entirety by reference.

FIELD OF THE INVENTION

The present invention relates to methods for treating AIDS-associated neurological disorders, inflammation and inflammation-associated disorders and to pharmaceutical compositions for use in practicing the method.

BACKGROUND OF THE INVENTION

The Acquired Immunodeficiency Syndrome (AIDS), caused by the human immunodeficiency virus type-1 (HIV-1), is one of the ten leading causes of death in the world (Koutsilieri, 2001). According to a June 2000 World Health Organization (WHO) report on global human immunodeficiency virus (HIV)/AIDS pandemic, nearly 35 million adults and 2 million children worldwide are infected with HIV and it is estimated that one third of the adults and more than one half of the children will develop a dementing illness.

This virus, transmitted by sexual contact or exposure to infected blood products, has to this point eluded attempts at eradication and continues to spread through human populations in both industrialized and non-industrialized nations. Although modern anti-viral medications may control viral replication and prolong life, there is currently no preventative vaccine and no examples of a cure (Glass, 2001).

A variety of neurological syndromes occur throughout the course of HIV infection, affecting the central nervous system, peripheral nervous system, and muscle. The sequelae of HIV infection can be categorized as either related to opportunistic infections of the nervous system, or as direct or indirect effects of the virus itself. Some disorders are manifested early and some late during the infectious process, and the pathological changes include inflammatory, demyelinating, and degenerative changes. This spectrum of diseases associated with a single virus infection is unique in virology.

Neurological disease occurs rarely at the time of initial infection with HIV, even before seroconversion, and prior to the profound immunosuppression of the latter stages of HIV infection. These early manifestations include aseptic meningitis or encephalitis, acute and chronic inflammatory demyelinating polyneuropathies, mononeuritis multiplex associated with peripheral nerve vasculitis, and HIV-associated polymyositis (McArthur, 1987).

Oxidative stress has been implicated in a variety of diseases and pathological conditions, including endothelial cell cytotoxicity, cancer, and coronary heart diseases, such as thrombosis and hyperlipemia (Addis, 1995). Recent studies have shown that elevated lipid peroxidation levels (oxidative stress) may play a role in the pathogenesis of Alzheimer's disease which includes a group of neurodegenerative disorders with diverse etiologies, but the same hallmark brain lesions (Practico, 1998).

Clinical studies have established that elevated plasma concentrations of LDL are associated with atherosclerosis, a most prevalent cardiovascular disease and the principle cause of heart attack, stroke and vascular circulation problems (Sarkkinen, 1993). It is believed that a reduction of atherogenic lipid peroxides, which are transported in the LDL fraction of blood serum, can reduce the risk of atherogenesis (Mazur, 1999). Antioxidants limit oxidative modification of LDL and consequently lower plasma concentrations of LDL, thereby acting as anti-atherogenic compounds (Sarkkinen, 1993). The oxidation of LDL has been reported as a model for testing the ability of polyphenols to act as antioxidants by breaking the peroxidative cascade described above (Rice-Evans, 1995).

A safe, relatively inexpensive, orally administered neuro protectant that reduces the sequelae of cerebral oxidative stress in the setting of HIV-associated brain disease would have great value as an adjunctive therapy. Benefits include those based on evidence regarding the effect of free-radical damage of oxidative stress on key organ systems. They include cerebral antioxidant activity with reduction of ongoing brain injury (Shi 1998; Treitinger 2000); antiviral effects (oxidative stress activates a transcription factor necessary for HIV replication, and phenols are effective in vitro against HIV-1: Ng, 1997); and antiatherosclerotic cardiovascular benefits. Of note, cardiovascular risk has become a concerning issue among HAART-treated individuals as the incidence of severe hyperlipidemia has increased (Lipodystrophy Syndrome). Oxidative stress inhibits the key enzyme responsible for the transfer and metabolism of cell-derived cholesterol via HDL. Antioxidant therapy increases the capacity of HDL for cholesterol uptake, and could lower cholesterol. In addition, antioxidants have been shown in vitro and in vivo to decrease oxidized LDL, strongly implicated as a mediator of endothelial damage of cardiovascular disease (Caruso 1999, Napoli 2001).

SUMMARY OF THE INVENTION

Accordingly, it is an object of the invention to provide, in one aspect, a method for treating an AIDS-associated neurological disorder in a subject in need of such treatment. The method includes administering to the subject a pharmaceutically effective amount of a treatment agent having hydroxytyrosol and oleuropein. In one embodiment, the weight ratio of hydroxytyrosol to oleuropein of between about 1:1 and about 200:1. In another embodiment, the weight ratio is between about 5:1 and about 100:1. In yet another embodiment, the weight ratio of hydroxytyrosol and oleuropein is between about 10:1 and about 50:1.

In a preferred embodiment, the treatment agent is prepared by a process comprising the steps of producing vegetation water from olives, adding acid to the vegetation water in an amount effective to produce a pH between about 1 and about 5, and incubating the acidified vegetation water until at least 75% of oleuropein originally present in the vegetation water has been converted to hydroxytyrosol.

An exemplary disorder for treatment is AIDS dementia. A preferred route of administration includes oral delivery.

In one embodiment, the administering further includes administering a second disease treatment agent. Administering the second treatment agent may be before or after administration of the first treatment agent. Alternatively, administering the second treatment agent is coincident with administering the first treatment agent. Preferably the second treatment agent is an antiretroviral agent.

In another embodiment, the first agent is administered at a dosage of between about 0.1 mg/kg and 2000 mg/kg per day. Preferably, the first agent is administered at a dosage of between about 0.3 mg/kg and 1 mg/kg per day. Even more preferably, the agent is administered at a dosage of about 0.6 mg/kg per day.

In one embodiment, the subject is a human. In another embodiment, the agent is dried to provide a powder extract. In yet another embodiment, the agent is in the form of a tablet, capsule, or pill.

In another aspect, the invention contemplates a method of treating an AIDS-associated neurological disorder in a subject in need of such treatment. The method includes administering to said subject a pharmaceutically effective amount of substantially purified hydroxytyrosol or a substantially purified mixture of hydroxytyrosol and oleuropein.

Another aspect of the invention includes a method of treating a subject having an inflammatory condition characterized by a detectable clinical symptom or change in a level of a biochemical marker with respect to the normal range of the marker. The method includes administering to the subject a dose of an olive plant extract treatment agent. In one embodiment, the extract has a weight ratio of hydroxytyrosol to oleuropein of between about 1:1 and about 200:1. In another embodiment, the weight ratio is between about 5:1 and about 100:1. Preferably the weight ratio is between about 10:1 and about 50:1.

The method further includes continuing said administration until there is observed a return of the marker level to the normal range or a desired change in the clinical symptom. The marker or the clinical symptom may be (i) the symptoms and markers in joint pain and swelling in the case of joint inflammation; (ii) elevated levels of C-reactive protein in the case of coronary inflammation; (iii) respiratory distress in the case of bronchial inflammation; and/or (iv) elevated CSF levels of isoprostanes or functional or psychofunctional indicators in the case of neuro-inflammation.

In one embodiment, the marker is a cytokine such as tumor necrosis factor-α, interleukin-1, interleukin-6, and/or interleukin-8.

In another embodiment, the marker is corticotrophin, cortisol and/or prolactin.

In one embodiment, the inflammatory condition is selected from the group consisting of rheumatoid arthritis, osteoarthritis, and other inflammatory conditions involving acute joint inflammation, chronic joint inflammation, or both.

The extract may be prepared by a process that includes (a) producing vegetation water from olives; (b) adding acid to the vegetation water in an amount effective to produce a pH between about 1 and about 5; and (c) incubating the acidified vegetation water until at least 75% of oleuropein originally present in the vegetation water has been converted to hydroxytyrosol.

The administration may include a method selected from the group consisting of oral delivery, intramuscular injection, intravenous injection, transdermal delivery, and/or transmucosal delivery. Preferably the the administering includes oral delivery.

In one embodiment of the invention, the administering further comprises administering a second disease treatment agent. The administering of the second treatment agent may be before, after or coincident with administration of the first treatment agent. The second treatment agent includes one or more of the components selected from the group consisting of glucosamine sulfate, chondroitin sulfate, sea cucumber extract, hydrolyzed shark cartilage, collagen II, and methylsulfonylmethane.

In one embodiment of the invention the agent or extract is administered at a dosage of between about 0.1 mg/kg and 2000 mg/kg per day. Preferably the agent or extract is administered at a dosage of between about 0.3 mg/kg and 1 mg/kg per day. More preferably, the agent is administered at a dosage of about 0.6 mg/kg per day.

In one embodiment, the subject is a human.

In another embodiment, the agent is dried to provide a powder extract.

In yet another embodiment, the agent is in the form of a tablet, capsule, or pill. Alternatively, the agent may be in the form of a liquid or liquid drops.

In a broader aspect, the invention provides a method of treating an inflammatory condition in a subject in need of such treatment, comprising administering to said subject a pharmaceutically effective amount of substantially purified hydroxytyrosol or a substantially purified mixture of hydroxytyrosol and oleuropein. In one embodiment, the inflammatory condition is in response to a condition selected from the group consisting of delayed type hypersensitivity reaction, a symptom of psoriasis, an autoimmune disease, organ transplant, pain, fever, and tissue graft rejection. Preferably, the autoimmune disease is selected from the group consisting of: Reynaud's syndrome, autoimmune thyroiditis, EAE, multiple sclerosis and lupus erythematosus.

In another embodiment, the inflammatory condition is in response to a condition selected from the group consisting of adult respiratory distress syndrome (ARDS), multiple organ injury syndromes secondary to septicemia or trauma, reperfusion injury of myocardial or other tissues, acute glomerulonephritis, reactive arthritis, dermatoses with acute inflammatory components, acute purulent meningitis or other central nervous system inflammatory disorders, thermal injury, hemodialysis, leukapheresis, ulcerative colitis, Crohn's disease, necrotizing enterocolitis, granulocyte transfusion associated syndromes, and cytokine-induced toxicity.

In yet another embodiment, the inflammatory condition results from a condition selected from the group consisting of asthma, psoriasis, skin sunburn, inflammatory pelvic disease, inflammatory bowel disease, urethritis, uvitis, senusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis and cholangititis.

In still another embodiment, the inflammatory condition is an acute inflammatory reaction. Alternatively, the inflammatory condition is an allergic inflammatory reaction.

These and other objects and features of the invention will be more fully appreciated when the following detailed description of the invention is read in conjunction with the accompanying FIGURE.

DETAILED DESCRIPTION OF THE INVENTION

I. Definitions

Figure 1:
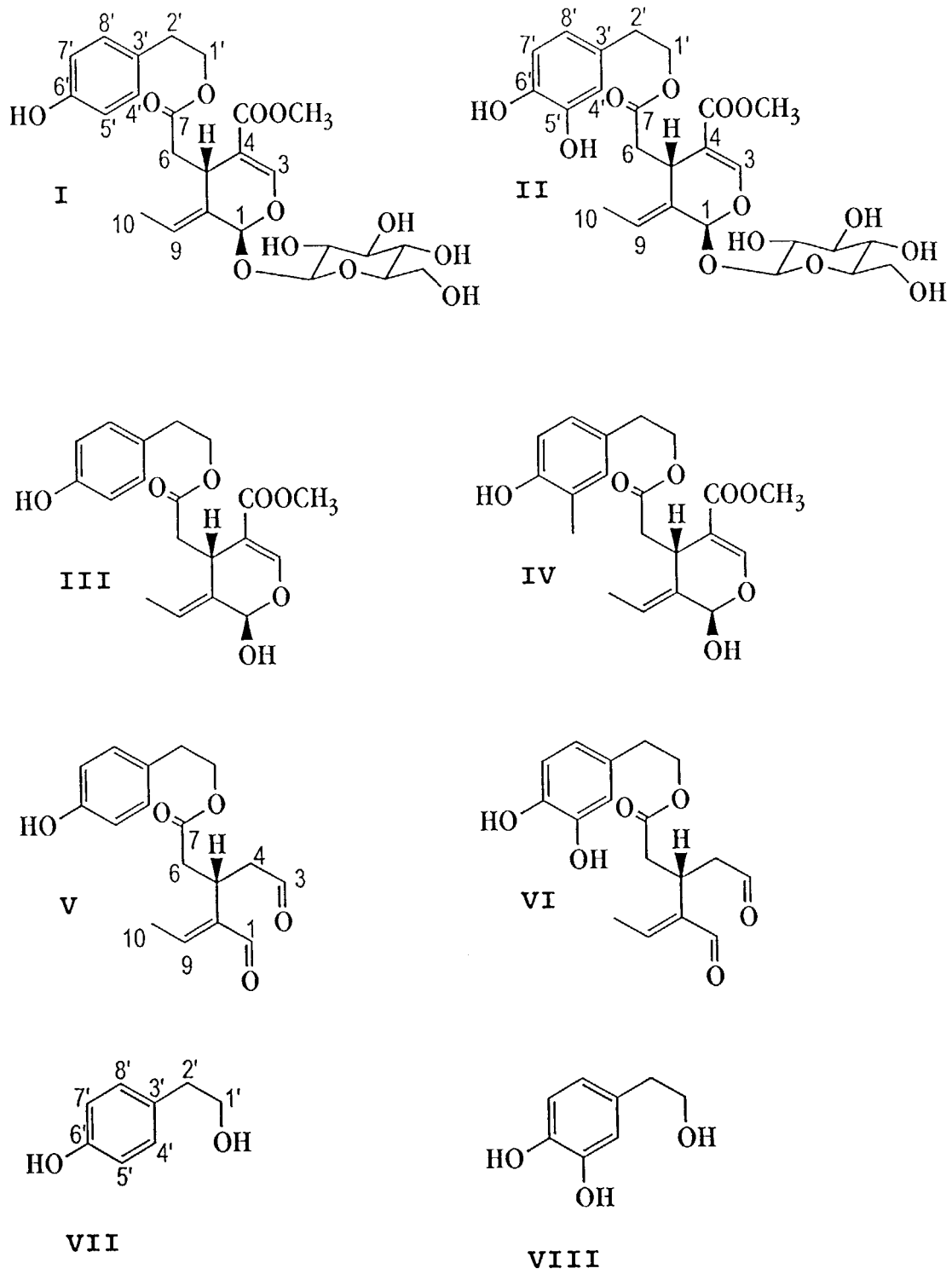
FIG. 1 shows the structures of phenolic compounds and their precursors detected in olive oil: ligstroside (I); oleuropein glucoside (II); aglycone of ligstroside (III); aglycone of oleuropein glucoside (IV); dialdehydic form of ligstroside aglycone laking a carboxymethyl group (V); dialdehydic form of oleuropein glucoside aglycone lacking a carboxymethyl group (VI); tyrosol (VII); hydroxytyrosol (VIII).

Unless otherwise indicated, all terms used herein have the same meaning as they would to one skilled in the art of the present invention. It is to be understood that this invention is not limited to the particular methodology, protocols, and reagents described, as these may vary.

The term "effective amount", as used herein, represents an amount of agent necessary to prevent or treat a subject susceptible to or suffering from an AIDS-associated neurological condition or an inflammatory response following administration to such subject. The active compound may be effective over a wide dosage range. It will be understood that the amount of the compound actually administered will be determined by a physician, in light of the relevant circumstances including the condition to be treated the age, weight, and response of the individual patient, the severity of the patient's symptoms, and the chosen route of administration.

As used herein, the term "treating" includes prophylaxis of a physical and/or mental condition or amelioration or elimination of the developed physical and/or mental condition once it has been established or alleviation of the characteristic symptoms of such condition.

By "oleuropein" is intended secoiridoid glucoside oleuropein (Structure II in FIG. 1).

By "tyrosol" is intended 4-hydroxyphenethyl alcohol (Structure VII in FIG. 1).

By "hydroxytyrosol" is intended 3,4-dihydroxyphenethyl alcohol (Structure VIII in the FIG. 1).

The term "substantially purified", as used herein, refers to a compound or compounds that are removed from their natural environment, isolated or separated, and are at least 60% free, preferably 75% free, more preferably 85% free, even more preferably 90% free, still more preferably 95% free, and most preferably 99% free from other components with which they are naturally associated.

II. Method of the Invention

The invention includes, in one aspect, a method of treating an AIDS-associated neurological disorder. Another aspect of the invention provides a method of treating inflammation or an inflammation-associated disorder. In practicing the method of the invention, the composition as described below, is preferably formulated as a tablet formulation, is preferably administered orally at a desired dose and dosing schedule.

The method of the invention employs phenolic compounds. Hydroxytyrosol and oleuropein are preferred phenols. The phenolic compounds may be synthesized or extracted and/or purified by methods known to those of skill in the art.

A. Olive-Derived Phenols

Preferably, the phenolic compounds are derived from olives that may be obtained from conventional and commercially available sources such as growers. A number of phenolic compounds are found in olives and olive oil, including relatively apolar, oil soluble phenolic compounds as well as relatively polar, water soluble phenolic compounds. In the context of the present invention both groups are denoted as phenols. Apolar phenols comprise the compounds oleuropein, ligstroside and their aglycons. Polar phenols comprise tyrosol, hydroxytyrosol, caffeic acid and vanillic acid.

The olive-derived phenolic compounds employed herein can be prepared by a number of methods known in the art. The olives may be processed by any suitable means to obtain the compositions described. In one embodiment of the invention, the olives are pressed to obtain a mixture including olive oil, vegetation water, and solid by-products. The phenolic compounds may be obtained directly from the mixture, or the mixture may be fractionated and/or purified to obtain the compounds of the invention. The compositions may be fractionated and/or purified by a number of methods known to those of skill in the art. Exemplary methods for fractionation include partitioning with an organic solvent, high pressure liquid chromatography (HPLC), or the use of supercritical fluids.

Exemplary methods for preparing phenolic compositions derived from olives in accordance with the invention may be found in co-owned U.S. Pat. No. 6,165,475, issued Dec. 26, 2000 and U.S. Pat. No. 6,197,308, issued Mar. 6, 2001, each of which is expressly incorporated by reference herein. An exemplary method for preparing hydroxytyrosol-rich compositions from olive vegetation water is found in co-owned U.S. patent application Ser. No. 09/944,744, filed Aug. 31, 2001, which is expressly incorporated by reference herein. Techniques suitable for concentrating and/or isolating oleuropein from aqueous and aqueous-alcoholic solutions are taught, for example, in U.S. Pat. No. 5,714,150, expressly incorporated herein by reference.

A preferred method of obtaining hydroxytyrosol and/or oleuropein is considered below:

1. Producing Vegetation Water

Preferably, the vegetation water is obtained from pitted olives. The olives processed according to the method disclosed herein may be pitted by any suitable means. Pits in the olives contain tyrosol which is an undesired component in the vegetation water and which may not be appreciably eliminated by the acid treatment described below. The pits may be separated from the pulp manually or in an automated manner as described below. Preferably, such means should be capable of segregating the pits without breaking them, which might otherwise cause higher concentrations of tyrosol in the vegetation water. In another embodiment, hydroxytyrosol is extracted from vegetation water obtained from olives that have not been pitted.

To produce vegetation water, olive pulp from the olives is first pressed to obtain a liquid-phase mixture including olive oil, vegetation water, and solid by-products. Thereafter, the vegetation water is separated from the rest of the liquid phase mixture and collected. Exemplary methods of obtaining vegetation water are described in the above-referenced, co-owned U.S. Pat. Nos. 6,165,475 and 6,197,308, both to R. Crea, each of which are expressly incorporated herein by reference in their entirety.

For purposes of commercial production, it may be desirable to automate various aspects of the invention. In this regard, one embodiment contemplates the use of an apparatus as disclosed in U.S. Pat. Nos. 4,452,744, 4,522,119 and 4,370,274, each to Finch et al., and each expressly incorporated herein by reference. Briefly, Finch et al. teach an apparatus for recovering olive oil from olives. Initially, olives are fed to a pulper that separates the olive pits from the olives to obtain a pitless olive meat. The meat is then taken up by an extraction screw that subjects the meat to an extraction pressure sufficient to withdraw a liquid phase, comprising oil, water and a minor proportion of olive pulp. The liquid phase is collected in a bin and then sent to a clarifying centrifuge that separates the pulp from the liquid phase to obtain a mixture comprising olive oil and vegetation water. A purifying centrifuge then separates the vegetation water and a small proportion of solid matter from the mixture to obtain an olive oil, substantially free of vegetation water, that is collected in a tank.

Additional devices that may be used in practicing the present invention are disclosed in Italian Patent Nos. 1276576 and 1278025, each of which is expressly incorporated herein by reference. As above, these devices can be used to separate the pulp from the pits prior to processing of the crushed olive pulp into oil, water, and solid residues.

2. Conversion of Oleuropein to Hydroxytyrosol

In one aspect of the invention, the oleuropein contained in the vegetation water is converted to hydroxytyrosol. The pH of the vegetation water may be decreased by the addition of acid (organic or inorganic), and the vegetation water allowed to incubate under conditions which promote hydrolysis of oleuropein to hydroxytyrosol. The sample may then be fractionated to separate hydroxytyrosol from other compounds.

In a preferred embodiment, the added acid is citric acid. The acid is added to the vegetation water to adjust the pH to 1-5, preferably 2-4. Solid citric acid can be added while continuously stirring in an amount of preferably about 25 to 50 pounds of acid per about 1000 liters of vegetation water. The pH of the resulting solution can be monitored, and further addition of acid may be necessary to achieve the desired pH.

The acid may also be an organic or inorganic acid other than citric acid. Exemplary acids which may be used in the present invention include the inorganic substances known as the mineral acids—sulfuric, nitric, hydrochloric, and phosphoric acids—and the organic compounds belonging to the carboxylic acid, sulfonic acid, and phenol groups. The addition of acid to the vegetation water serves several purposes: (i) it stabilizes the vegetation water from rapid oxidation by the air/oxigen; (ii) it prevents fermentation (bacteria) of the vegetation water; and (iii) it hydrolizes the oleuropein, converting it to hydroxytyrosol. In one embodiment, the mixture is allowed to incubate until hydroxytyrosol is 75-90% of the total combination of tyrosol and hydroxytyrosol, and substantially none of the oleuropein in the original mixture remains.

3. Purification of Hydroxytyrosol

Following the conversion of oleuropein to hydroxytyrosol, the vegetation water may be fractionated by a number of methods known in the art. Alternatively, vegetation water may be fractionated prior to treatment with acid.

Vegetation water obtained as described above provides a solution which is rich in low molecular weight polyphenols, particularly hydroxytyrosol and a small amount of tyrosol. The concentration of hydroxytyrosol in the processed water may range from 4-5 grams per liter to 10-15 grams per liter depending upon the degree of dilution during the olive oil extraction. In one embodiment, the invention provides a method of extraction or purification that selectively enriches the content of hydroxytyrosol without the addition of contaminants. Thus, the major polyphenolic component, hydroxytyrosol, is isolated from other members of the polyphenolic family, impurities, suspended solids, tannins, and other molecules contained in the vegetation water. Hydroxytyrosol may therefore be produced in a purity and quantity not readily available by current synthetic or natural extraction methods.

B. Treatment of AIDS-Associated Neurological Conditions

In accordance with the present invention, there are provided therapeutic methods for treating a variety of conditions related to nervous system disorders.

In one aspect, the invention method comprises administering to a subject in need thereof an effective amount of a treatment agent having a weight ratio of hydroxytyrosol to oleuropein of between about 1:1 and about 200:1.

In one embodiment of the invention, the treatment agent is targeted against neurological conditions associated with AIDS. The neurological conditions contemplated for treatment are, in one embodiment, direct or indirect effects of the HIV virus itself. Alternatively, the neurological conditions treated according to the method of the invention are related to opportunistic infections of the nervous system. Preferred AIDS-associated neurological conditions for treatment are as follows:

1. ADC

HIV-1 Associated Dementia, also known as AIDS Dementia Complex (ADC), HIV/AIDS encephalopathy or encephalitis, subacute encephalitis, progressive dementia, HIV/AIDS Related Brain Impairment and AIDS Related Dementia, is a clinical diagnosis based on signs and symptoms of cognitive decline and fine motor dysfunction in the setting of HIV-1 infection, after exclusion of other etiologies. ADC may be progressive or relatively static. In the era of highly-active antiretroviral therapy (HAART), the incidence of fulminant ADC has declined; however, the incidence of a more insidious and protracted dementia, with higher CD4 counts, appears to be increasing (Dore, 1999).

Despite more than a decade of intensive research, the precise pathophysiology of ADC remains elusive. On pathology, atrophy and white matter pallor is observed usually without frank demyelination. Despite widespread scarring (gliosis) and neuronal cell loss, HIV-1 does not directly infect neuronal cells. HIV-1 is found only in macrophages in the brain, and degree of macrophage infiltration, rather than brain viral load, corresponds best to dementia severity (Glass, 1995). Radiographically, the diagnosis is supported by characteristic changes in subcortical and periventricular white matter ("HIV encephalitis"), as well as global cerebral atrophy.

Hence, ADC is considered an "indirect" effect of HIV infection: nervous system injury is driven primarily by the neuroimmunologic host response (Nottet, 1995). While some viral products are neurotoxic in brain cell cultures, it appears that proinflammatory molecules, secreted by or induced by macrophages, are the main effectors of ongoing brain injury. Toxic synergies among viral protein products (viz. Tat) and macrophage-derived cytokines (viz. TNF-α), interleukins (viz. IL-6), and oxygen free-radical reactions (viz. peroxynitrite) appear to lead to enhanced vulnerability to oxidative stress in the AIDS brain, resulting in massive cell death (Shi, 1998; Lipton, 1995).

There is no approved treatment for ADC. Cognitive improvement may be observed with aggressive antiretroviral therapy in some treatment naïve, or under treated, patients with ADC (Cohen, 2001). Pathologic observations indicate that HIV encephalitis remains a common finding (Masliah, 2000). HAART regimens, while perhaps attenuating the severity of dementia, do not appear to prevent HIV-associated brain injury.

The neurological symptoms associated with ADC have been treated with certain drugs that have a number of shortcomings. For example, the psychosis associated with HIV dementia has been treated with haloperidol and thioridazine. Molindone has been used for psychotic and delirious HIV dementia patients. Methylphenidate has been used for treatment of depression associated with ADC. Electro-convulsive therapy has been used for HIV-induced stupor. All of these treatments serve to ameliorate symptoms of ADC. None treat ADC itself.

The conditions treated with the treatment agents include, according to one embodiment of the invention, ADC and the various symptoms with which ADC is associated. An exemplary method of treating ADC is described in Examples 1-3. The treatment agent formulations may be administered to achieve a therapeutic effect and slow or counteract the progression of ADC or they can be administered prophylactically to patients not yet exhibiting ADC but exposed to the HIV virus.

2. HIV-Associated Myelopathy

HIV-associated myelopathy occurs in approximately 20% of patients with late stage AIDS and is clinically characterized by progressive spasticity and loss of proprioception, predominantly in the lower extremities. Pathologically these findings correlate with vacuolar changes that are most prominent in the posterior and lateral columns of the thoracic spinal cord (termed vacuolar myelopathy) and are morphologically similar to those seen in vitamin $B_{12}$ deficiency (Petito et al, 1985). Autopsy studies have shown that vacuolar myelopathy is found in up to 50% of patients dying with AIDS, with only the more severe cases showing symptoms during life (Dal Pan, 1994).

Thus, according to one embodiment of the invention, HIV-associated myelopathy and the symptoms with which HIV-associated myelopathy is associated are treated.

3. Peripheral Neuropathy

According to another embodiment, this invention provides a therapeutic method for treating a patient suffering from peripheral neuropathy. This method involves administering to the patient an effective peripheral neuropathy-treating amount of one or more of the treating agents or pharmaceutical compositions described. In yet another embodiment, this invention provides a prophylactic method for protecting a patient susceptible to peripheral neuropathy. This method involves administering to the patient an effective peripheral neuropathy prophylactic amount of one or more of the pharmaceutical compositions or treating agents of the invention.

Peripheral neuropathy is a very common and disabling problem encountered in HIV infection. It develops primarily in relatively advanced patients with low CD4 counts, and may be exacerbated by the neurotoxicity of several of the drugs commonly used to treat HIV including DDC, DDI, and D4T. However, it is clear that the viral infection itself results in a typical symmetric, painful, distal sensory neuropathy. This entity almost always presents with variable loss of sensation in the feet and a variety of uncomfortable sensations of swelling, prickling, throbbing or other painful sensations in the feet. This may extend up the legs as it worsens and may eventually start to effect the hands. It occurs in around 20% of AIDS patients, and similar symptoms occur in an even greater number when the drug induced neuropathy is included.

Treatment of neuropathic pain such as is encountered in neuropathy is notoriously difficult. Minimizing neurotoxic drugs, optimizing diet, assuring that there are no contributing vitamin deficiencies (especially $B_{12}$ and thiamine) are important first steps. Alcohol is often a neurotoxin, and continued heavy alcohol use may worsen symptoms. Routine analgesics such as aspirin and ibuprofen generally provide little relief. Even narcotics may not fully relieve this kind of pain.

4. Cytomegalovirus Encephalitis and Radiculomyelitis

Cytomegalovirus is a frequent secondary viral infection in AIDS patients, causing retinitis in up to 40%. Autopsy studies indicate that as many as 20-30% of AIDS patients have CMV encephalitis pathologically, while probably almost 10% develop a clinical neurologic deterioration that is probably the result of CMV. There are two general neurologic syndromes which may occur separately, or in conjunction with each other. The first is the result of CMV attacking the spinal roots and cord resulting in a rapid loss of function of bladder, saddle anesthesia and legs weakness with variable degree of pain and paralysis. The CSF typically has an inflammatory pattern, and sometimes CMV can be cultured from the CSF. Evaluation of the CSF for CMV DNA reveals abundant viral DNA.

The other presentation may mimic a more aggressive form of AIDS dementia complex, with symptoms of dementia developing over just a few weeks time, sometimes associated with cranial nerve abnormalities affecting vision, hearing and balance that would be unusual for HIV alone. The spinal fluid is often bland in this disorder, but CSF PCR for CMV DNA is positive, and strongly supports the diagnosis when such a clinical pattern is seen. This disorder is generally rapidly fatal over a period of just 4-8 weeks. Thus, the conditions treated with the treatment agents and pharmaceutical compositions of the invention include, according to one embodiment, CMV encephalitis and radiculomyelitis.

5. Progressive Multifocal Leukoencephalopathy (PML)

PML is a lethal secondary viral infection mostly occurring in AIDS patients with advanced immunodeficiency. At present, approximately 6% of AIDS patients die with this condition. The JC virus is a ubiquitous virus, able to enter the brain and lytically infect oligodendrocytes (the cells making myelin in the brain). Thus, demyelination of the brain results, causing a wide variety of focal neurologic symptoms including weakness, loss of sensation, visual loss, changes in balance and coordination. Because it is usually relentlessly progressive, severe neurologic disability develops over a period of 2-6 months with death following rapidly from general disability. According to one embodiment of the invention PML is a condition treated with the treatment agents or pharmaceutical compositions described.

6. Other Neurological Diseases

Additional neurological diseases and disturbances contemplated for treatment by the method of the invention include, but are not limited to, Alzheimer's disease; Parkinson's disease; motor neuron diseases such as amyotrophic lateral sclerosis (ALS), Huntington's disease and syringomyelia; ataxias, dementias; chorea; dystonia; dyslinesia; encephalomyelopathy; parenchymatous cerebellar degeneration; Kennedy disease; Down syndrome; progressive supernuclear palsy; DRPLA, stroke or other ischemic injuries; thoracic outlet syndrome, trauma; electrical brain injuries; decompression brain injuries; multiple sclerosis; epilepsy; concussive or penetrating injuries of the brain or spinal cord; brain injuries due to exposure of military hazards such as blast over-pressure, ionizing radiation, and genetic neurological conditions.

By "genetic neurological condition" is meant a neurological condition, or a predisposition to it, that is caused at least in part by or correlated with a specific gene or mutation within that gene; for example, a genetic neurological condition can be caused by or correlated with more than one specific gene. Examples of genetic neurological conditions include, but are not limited to, Alzheimer's disease, Huntington's disease, spinal and bulbar muscular atrophy, fragile X syndrome, FRAXE mental retardation, myotonic dystrophy, spinocerebellar ataxia type 1, dentatorubral-pallidoluysian atrophy, and Machado-Joseph disease.

As described above, presently preferred conditions for treatment in accordance with the present invention include AIDS-associated neurological disorders. An especially preferred condition for treatment in accordance with the present invention includes ADC.

The present invention also relates to combinational therapeutic methods for treating AIDS and AIDS-associated neurological disorders. Combinations of agents contemplated for use in the practice of the present invention are administered to a host in need of such treatment by employing an effective amount of a combination of a least one treating agent useful for the treatment of infectious viral conditions, and at least one AIDS-associated neurological disorder treatment agent as described above. Exemplary HIV antivirals with good CNS penetration include zidovudine, D4T, nevirapine, and abacavir.

C. Oxidative Stress

Use of the treatment agents or pharmaceutical compositions of the invention, according to one aspect, in preparations to be administered via different carriers will protect the body against oxidative stress and prevent the outburst of different diseases caused by such oxidative stress.

It is known that free radicals (oxidative stress) of different types are associated with a range of diseases such as ischemic or reperfusion injury, thrombosis and embolism, atherosclerosis, allergic/inflammatory conditions such as bronchial asthma and rheumatoid arthritis, diseases caused by ionizing radiation or ultra violet light, conditions related to neurodegenerative diseases for instance Parkinson's disease and Alzheimer's disease, ageing, apoptosis, necrosis and cirrhosis, cataract, physical stress, diabetes, autoimmune diseases, intoxications, colitis, hematocrosis, neoplasms and toxicity of antineoplastic or immuno suppressive agents diseases, premature aging or consequences of viral or bacterial infections and endogeneous or exogeneous chemicals present in air, food, general environmental contamination or lifestyle related exposure. Lipid peroxidation or DNA-oxidation caused by excess generation of radicals can constitute significant damaging pathways in the above conditions and diseases.

Oxidative stress can be chemically, physically or biologically induced. Chemically induced oxidative stress is caused by a compound which gives rise to a tissue damage. Physically induced stress is caused by e.g. 1) radiation, such as radioactive or ionizing radiation or UV radiation; 2) by physical blockage of blood flow; biologically induced oxidative stress is the defense by the body itself, with over-reaction of oxidases in phagocytes, extra and intra cellular, one example is HIV patients. Other examples are asthma, rheumatoid arthritis, diabetes etc, cf. above.

Different conditions such as inflammations, infections, gamma-radiation, UV radiation and deficiency of vitamins/ antioxidants give rise to oxidative stress which leads to the different conditions and diseases stated above.

Thus, the invention includes, in one aspect, a method of treating oxidative stress in a person in need thereof, comprising administering to said subject a pharmaceutically effective amount of substantially purified hydroxytyrosol or a substantially purified mixture of hydroxytyrosol and oleuropein. The oxidative stress condition may be selected from the group consisting of an inflammatory response, coronary heart disease, and AIDS-associated neurological disorders.

D. Biological Testing

The effectiveness of a given phenol in treating an AIDS-associated neurological condition may be determined by methods known in the art.

1. Neuropsychological Testing

Cognitive evaluation of subjects may be determined by methods known in the art. For example, cognitive evaluation of HIV-1 infected patients may be performed using the tests as previously described by Ryan et al. (2001). Briefly, these tests assess member (Rey Auditory Learning Test), psychomotor speed (Trail-making), gross and fine motor functioning (Symbol Digit Substitutions, Grooved Pegboard), abstract thinking (Stroop Coor Interference), and mood (Center for Epidemiological Studies Depression Scale, Profile of Mood States).

The results of the tests may be analyzed to create a Z score by comparing each patient's performance to a mean score based on education- and age-adjusted normative data. An exemplary neuropsychological test is the NPZ-8 test utilized in Example 1 below.

2. Macrophage Activation

HIV is found in macrophages in the brain, and degree of macrophage infiltration corresponds well to dementia severity (Adamson, 1999; Glass, 1995). Blood-borne macrophages and/or CD4+ T lymphocytes can carry the virus into the brain and transport it to perivascular and parenchymal blood-derived macrophages and microglia (Bossi, 1998; Ellis, 1997; Brew, 1996).

Surrogate markers of macrophage activation in serum and/ or CSF may be identified by methods known in the art.

3. HIV-1 Viral Load

In one embodiment of the invention, the pharmaceutical composition of the invention is administered to HIV-infected patients in amounts and for a time sufficient to induce a clinically significant decrease in HIV viral load. HIV viral load may be measured by any method known to those of skill in the art. An exemplary method of measuring HIV viral load is by determining the level of HIV-RNA (measured in copies per ml) detectable by PCR in the plasma, serum, and/or CSF of an HIV-infected patient, as described in U.S. Pat. No. 6,309,632.

4. Additional Tests

In one embodiment of the invention, neural cell culture systems or in vivo biological tests may be used for determining the efficacy of the compositions in reversing neurotoxicity which mimics that observed with ADC, as described in International Patent Application WO 97/38684.

Additional tests contemplated by the invention include: measurement of isoprostane F2, a marker of oxidative stress and lipid peroxidate; plasma cholesterol and HDL; and CSF concentration of mono and polyphenol metabolites. Methods for performing these tests are known to those of skill in the art.

E. Treatment of Inflammation or Inflammation-Associated Conditions

As noted above, in accordance with another aspect of the invention, there are provided therapeutic methods for treating a variety of conditions related to inflammation or inflammation-associated disorders.

One role of the inflammatory response serves the purpose of eliminating harmful molecules from the body. A wide range of pathogenic insults can initiate an inflammatory response. These include autoimmune stimuli, infections, allergens, immune response to transplanted tissue, noxious chemicals, toxins, ischemia/reperfusion, hypoxia, and mechanical and thermal trauma. Typically, inflammation is a very localized response that serves to expulse, attenuate by dilution, and isolate the damaging agent and injured tissue. The body's response becomes an agent of disease when it results in inappropriate injury to host tissues in the process of eliminating the targeted agent, or responding to a traumatic insult.

Inflammation is a component of pathogenesis in a number of vascular diseases or injuries, including atherosclerosis. Blake, G J and Ridker, P M (2002) *J Internal Medicine* 252:283-294. The cells involved with inflammation include leukocytes (i.e., the immune system cells—neutrophils, eosinophils, lymphocytes, monocytes, basophils, macrophages, dendritic cells, and mast cells), the vascular endothelium, fibroblasts, vascular smooth muscle cells, and myocytes.

The release of inflammatory cytokines such as tumor necrosis factor-alpha (TNF-α) by leukocytes is a means by which the immune system combats pathogenic invasions, including infections. TNF-α stimulates the expression and activation of adherence factors on leukocytes and endothelial cells, primes neutrophils for an enhanced inflammatory response to secondary stimuli and enhances adherent neutrophil oxidative activity. In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative and nonoxidative inflammatory activity. Inappropriate and over-release of cytokines can produce counterproductive exaggerated pathogenic effects through the release of tissue-damaging oxidative and nonoxidative products. For example, TNFα can induce neutrophils to adhere to the blood vessel wall and then to migrate through the vessel to the site of injury and release their oxidative and non-oxidative inflammatory products.

Thus, the method of the present invention includes, in one aspect, a method of treating an inflammatory condition in a subject in need of such treatment. The method includes administering to the subject a pharmaceutically effective amount of substantially purified hydroxytyrosol or a substantially purified mixture of hydroxytyrosol and oleuropein.

The subject may have an inflammatory condition characterized by a detectable clinical symptom or change in a level of a biochemical marker with respect to the normal range of the marker.

A dose of an olive plant extract treatment agent having a weight ratio of hydroxytyrosol to oleuropein of between about 1:1 and about 200:1 is administered to the subject. Preferably, the weight ratio is between about 5:1 and about 100:1. More preferably, the weight ratio is between about 10:1 and about 50:1. The administration is continued until there is observed a return of the marker level to the normal range, a desired, measurable decrease in the level of the marker, or a desired change in the clinical symptom.

The marker or the clinical symptom may include any number of markers or clinical symptoms which are generally known in the art to be associated with inflammation. Preferably, the symptoms and markers are associated with specific types of inflammation. These include (i) the symptoms and markers in joint pain and swelling in the case of joint inflammation; (ii) elevated levels of C-reactive protein in the case of coronary inflammation; (iii) respiratory distress in the case of bronchial inflammation; and (iv) elevated CSF levels of isoprostanes or functional or psychofunctional indicators in the case of neuro-inflammation. The marker may be a cytokine, such as TNF-α, interleukin-1, interleukin-6, and/or interleukin-8. Other markers include corticotrophin, cortisol and/or prolactin.

In the case of joint inflammation, the inflammatory condition may be rheumatoid arthritis, osteoarthritis, and/or other inflammatory conditions involving acute joint inflammation, chronic joint inflammation, or both.

Additional inflammatory conditions that may be treated with the agent or extract of the invention include conditions such as delayed type hypersensitivity reaction, a symptom of psoriasis, an autoimmune disease, organ transplant, pain, fever, or tissue graft rejection. Exemplary autoimmune diseases are Reynaud's syndrome, autoimmune thyroiditis, EAE, multiple sclerosis or lupus erythematosus.

Additional exemplary inflammatory conditions include adult respiratory distress syndrome (ARDS), multiple organ injury syndromes secondary to septicemia or trauma, reperfusion injury of myocardial or other tissues, acute glomerulonephritis, reactive arthritis, dermatoses with acute inflammatory components, acute purulent meningitis or other central nervous system inflammatory disorders, thermal injury, hemodialysis, leukapheresis, ulcerative colitis, Crohn's disease, necrotizing enterocolitis, granulocyte transfusion associated syndromes, cytokine-induced toxicity, asthma, psoriasis, skin sunburn, inflammatory pelvic disease, inflammatory bowel disease, urethritis, uvitis, senusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis and cholangititis.

The inflammatory condition may be an acute inflammatory reaction or an allergic inflammatory reaction.

The treatment agent mixture may be prepared by any number of methods known in the art. Preferably, the treatment agent is an extract prepared by the process described in Section II.A. above. A particularly preferable method of preparing the treatment agent involves producing vegetation water from olives; optionally adding acid to the vegetation water in an amount effective to produce a pH between about 1 and about 5; and incubating the acidified vegetation water until a substantial portion, e.g. at least 75%, of oleuropein originally present in the vegetation water has been converted to hydroxytyrosol.

A wide variety of administration methods are contemplated by the present invention and discussed in further detail in Section III below. These include oral delivery, intramuscular injection, intravenous injection, transdermal delivery, and transmucosal delivery. Oral delivery is preferred.

The compounds of this invention are useful in the treatment or alleviation of inflammation, other inflammation associated disorders, such as arthritis, neurodegeneration and colon cancer, in mammals, preferably humans, dogs, cats or livestock animals.

The amount of therapeutically active compound that ss administered and the dosage regimen for treating a disease condition with the compounds and/or composition of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg/kg body weight, preferably in the range of about 0.3 to 50 mg/kg and most preferably about 0.6 mg/kg. A daily dose can be administered in one to four doses per day. In one embodiment a daily dose of 20 mg is delivered in 4 doses of 5 mg each.

The active agent or extract of the present invention may be administered in combination with other agents. The agents may be administered before, after, and/or during administration with the primary treatment agent. Preferable combinatorial agents include glucosamine sulfate, chondroitin sulfate, sea cucumber extract, hydrolyzed shark cartilage, collagen II, and methylsulfonylmethane.

Additional inhibitors of mediators of inflammation contemplated for use in combination with the active agent or extract of the present invention include matrix metalloproteinase inhibitors, aggrecanase inhibitors, TACE inhibitors, leucotriene receptor antagonists, IL-1 processing and release inhibitors, IL-1 ra, H (1)-receptor antagonists; kinin-B (1)- and B (2)-receptor antagonists; prostaglandin inhibitors such as PGD-, PGF-PGI (2)-, and PGE-receptor antagonists; thromboxane A (2)(TXA2-) inhibitors; 5- and 12-lipoxygenase inhibitors; leukotriene LTC (4)-, LTD (4)/LTE (4)-, and LTB (4)-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

III. Pharmaceutical Compositions

The therapeutic compositions described herein may be administered subcutaneously, intravenously, parenterally, intraperitoneally, intradermally, intramuscularly, topically, enteral (for example, orally), rectally, nasally, buccally, vaginally, by inhalation spray, by drug pump or via an implanted reservoir in dosage formulations containing conventional nontoxic, physiologically (or pharmaceutically) acceptable carriers or vehicles.

In a specific embodiment, it may be desirable to administer the agents of the invention locally to a localized area in need of treatment; this may be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes; such as sialastic membranes or fibers.

When it is desirable to direct the drug to the central nervous system, techniques which can opportunistically open the blood brain barrier for a time adequate to deliver the drug there through can be used. For example, a composition of 5% mannitose and water can be used. The present invention also provides pharmaceutical compositions. Such compositions comprise a therapeutically (or prophylactically) effective amount of the agent, and a physiologically acceptable carrier or excipient. Such a carrier includes, but is not limited to, saline, buffered saline, dextrose, water, glycerol, ethanol, and combinations thereof. The carrier and composition can be sterile. The formulation should suit the mode of administration.

Suitable pharmaceutically acceptable carriers include but are not limited to water, salt solutions (for example, NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, for example, lubricants, preservatives, stabilizers, wetting agents, emulsifiers, salts for influencing osmotic pressure, buffers, coloring, flavoring and/or aromatic substances and the like which do not deleteriously react with the active compounds.

The compositions, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The compositions can be formulated in accordance with the routine procedure as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, enemas, lotions, sols, liniments, salves, aerosols, etc., which are, if desired, sterilized or mixed with auxiliary agents, for example, preservatives, stabilizers, wetting agents, buffers or salts for influencing osmotic pressure, etc. The drug may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

The amount of agent or agents which will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

From the foregoing, it can be seen how various objects and features of the invention are met.

IV. EXAMPLES

The following examples further illustrate the invention described herein and are in no way intended to limit the scope of the invention.

Example 1

Study Procedures

This is a prospective, randomized, double-blind, placebo-controlled six-week parallel study of up to 32 subjects with HIV-associated cognitive dysfunction who have been on a stable medication regimen (antiretroviral and other medications) for at least 8 weeks. Subjects will be stratified at randomization, based on a "biased coin" paradigm, with regard to HIV-1 Viral Load <50,000 copies/ml versus equal to or greater than 50,000 copies/ml, to insure the two groups are balanced with regard to this important clinical variable. Subjects will receive either the active ingredient (20 mg total phenols) or identical placebo tablets (provided by the manufacturer) to be taken orally. Subject, Investigator and Sponsor will be blinded to treatment assignment until study completion.

At baseline and at Study Week 6, neuropsychiatric testing (NPZ-8), neurological examination, urinary F2 Isoprostane, serum beta-2 microglobulin, HIV-1 Viral Load, CD4 lymphocyte count, serum chemistries (electrolytes, renal and liver function tests), coagulation profile, and lipid profile will be obtained. Approximately 15 mL of blood will be obtained at baseline and at 6 weeks from each subject. A urine sample of 20 mL will be obtained at these time points. At study weeks 2 and 4, subjects will be contacted by the study assistant by telephone with regard to any changes in status or adverse events. Adverse events will be evaluated by the PI as appropriate.

It is anticipated that up to 8 subjects will consent to lumbar puncture at baseline and at 6 weeks for assessment of CSF F2 Isoprostane, B2 microglobulin, CSF viral load, and measurement of Hydroxytyrosol-derived metabolites. LP will be performed by the PI.

The PI, for example, a board-certified neurologist, neuro-AIDS specialist and PI in previous ADC trials, will perform patient selection and neurologic examinations. The neuropsychiatric battery, the NPZ-8, takes about 30 minutes to administer, and has been validated in the ADC population and is the most commonly used instrument in ADC treatment trials. The neurologic examination will take approximately 30 minutes. The baseline and follow-up visits should take no more than 90 minutes each, including phlebotomy, for the average subject. Each follow-up telephone call will take, on average, approximately 10 minutes.

Urinary and, if available, CSF F2-isoprostane assays will be performed at a state-of-the-art laboratory which performs this and other prostaglandin assays. CSF phenol (hydroxytyrosol) concentrations will be measured, blind to treatment assignment of subjects Subjects willing to undergo baseline and follow-up lumbar puncture will be consented separately. No subject will be denied participation in the study because of reluctance to undergo LP. The procedure typically takes 20 minutes. Subjects can, if they wish, remain supine for a period of time after the procedure. However, contrary to common belief, remaining supine post LP is not associated with reduction in incidence (10%) of post LP headache. Should a post LP headache occur, the subject will be offered treatment (blood patch: >85% success rate).

Example 2

Data Analysis

Safety data will be summarized descriptively for the two groups—active vs. placebo—using COSTART terms for mapping adverse events.

Change scores in laboratory safety evaluations (serum electrolytes, BUN, creatinine, CBC and differential, PT, PTT, platelets, total and HDL cholesterol, AST, ALT, total bilirubin) will be summarized.

The primary efficacy variable—difference in group mean concentrations of Isoprostane F2 at Study Week 6 compared with baseline—will be analyzed using 2-sided student's T test, with normalization of baseline concentrations. Because a normal distribution of this variable cannot be assumed, a Wilcoxin signed rank test will also be used to examine the difference in Iso-F2 from baseline to Study Week 6 in individual subjects, ranked according to magnitude, with determination of the test statistic to compare the treatment versus placebo groups. With regard to secondary variables, these approaches will be used to examine differences from baseline in B2 microglobulin and HIV-1 viral load in serum and, where possible, in urine. Descriptive summary statistics will be provided for subgroups. All analyses will be done by an independent third party using SAS software.

Example 3

Subject Selection

All subjects will be HIV-1 seropositive by Elisa, confirmed by Western Blot. Rationale for studying this population: there is no proven treatment for ADC or HIV-associated cognitive motor syndrome. The brain injury that occurs as a result of HIV-1 infection continues to afflict AIDS patients, despite highly-active antiretroviral therapy. As HIV-1 infected individuals live longer, ADC prevalence, and perhaps incidence, will likely rise.

Up to 32 subjects will be enrolled. It is expected that full data will be then available for approximately 12 subjects in each group, talking into account a 20% drop out rate typical from an ADC clinical trial. The sample size is reasonable for a pilot safety and tolerability study. Statistical significance is not expected for the primary efficacy endpoint in this small study; a trend towards group differences may be detected.

HIV-1 seropositive men and women over the age of 18, with signs and symptoms of HIV-associated cognitive-motor syndrome or frank ADC (Stage 0.5-2 Memorial Sloan Kettering AIDS Dementia Scale) for at least 3 months, and a Karnovsky score >50 (able to care for most of daily needs, but may need some assistance) will be eligible for enrollment. Subjects will have been on a stable regimen of antiretroviral and any other medical treatments for at least 3 months, and will reasonably be expected to remain on their current regimen for the duration of the study. Subjects in other investigational protocols or agents will be excluded. Other causes of cognitive impairment, such as thyroid disease, vitamin deficiency, testosterone deficiency (if male), neurosyphilis, other CNS disease, uncontrolled epilepsy, untreated depression, hepatic or uremic encephalopathy, traumatic brain injury or drug or alcohol abuse will be excluded per standard evaluation prior to enrollment. If an appropriate workup has not been performed, the potential subject will be referred back to his or her primary provider for evaluation. Subjects will be ambulatory, and have no active clinically significant systemic disease (other than HIV) that would, in the PI's judgment, preclude safe participation or compliance with the protocol.

Initial results from the above examples 1-3 showed a statistically significant favorable change in 8-isoprostane levels in the urine.

Example 4

Arthritis Studies

Test a group of individuals with Rheumatoid Arthritis and a group with Osteoarthritis with the stress reactivity protocol, before and after 4 weeks of active agent (20 mg total phenols) supplementation and compare to controls over the same time period with no supplementation. Measurements will include heart rate, blood pressure, cortisol, ACTH, PRL, cytokines, and CRP.

Test individuals with Rheumatoid Arthritis, before and after 10 weeks of active agent supplementation and compare to a group doing water aerobic exercise and a control group that does no intervention. Measurements will include assessment of disease activity, prostaglandins, cortisol, PRL, CRP, mood changes, fitness measures, and endurance.

Test individuals with Rheumatoid Arthritis, with and without active agent supplementation for four weeks, and examine their acute phase response to an exercise strength test using a leg press set at 70% of the 1 Rep Max. Measurements will include cortisol, PRL, CRP, and a panel of inflammatory cytokines.

Evaluate increasing concentrations of active agent in a collagent-induced arthritis mouse model at 1.3 mg, 13 mg and 130 mg/mouse; with and without Cox-2 inhibitors. The positive control involves treatment with Cox-2 inhibitors, NSAID, or steroids at the highest dose levels. Parameters such as swelling determined by ankle width measurement; histopathological score involving subsynovial inflammation characterized by mononuclear cell resembling nodule formation, pannus formation, bone erosion and synovial hyperplasia; radiological score; and cytokine analysis score measuring levels of TNF-α, IL-1, JE/CCLE (mouse Monococyte Chemotactic Protein-1), and IL-8.

Use of the mouse model as an acute inflammation/injury model to evaluate inhibitors that increase survival by reducing the levels of TNF-α and IL-1 induced by a single intraperitoneal injection of 50 μg of LPS and D-Galactosamine (600 mg/kg). In this model, mice are treated with the active agent (1.3; 13; and 130 mg/mouse) 12 hours prior to injection with LPS/D-Gal i.p. Survivial of mice is followed for 72 hours following injection with LPS/D-Gal. At 72 hours, blood is collected from all mice by retro-orbital puncture for measurement of TNF-α and IL-1 levels by ELISA.

Additional exemplary studies include TNF-α and IL-1 production induced by LPS by THP-1 monocytes, IL-8 production by fibroblasts; the effects of the active agent on the levels of superoxide and hydrogen peroxide production from human neutrophils; and basal levels of Cox-1 and LPS-induced levels of Cox-2 regulation in monocytes and fibroblasts with active agent added prior to LPS addition.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described with respect to particular embodiments, it will be apparent to those skilled in the art that various changes and modifications can be made without departing from the invention.

It is claimed:

1. A method of treating a subject having an inflammatory condition characterized by a detectable clinical symptom or change in a level of a biochemical marker with respect to the normal range of the marker, the method comprising:

administering to the subject a dose corresponding to between about 0.1 mg/kg body weight and 2000 mg/kg body weight daily of a first treatment agent comprised of an olive plant extract having a weight ratio of hydroxytyrosol to oleuropein of between about 1:1 and about 200:1; and continuing said administration until there is observed a return of the marker level to the normal range or a desired change in the clinical symptom, where the marker or the clinical symptom is selected from the group consisting of
   (i) elevated levels of C-reactive protein in the case of coronary inflammation;
   (ii) respiratory distress in the case of bronchial inflammation; and
   (iii) elevated CSF levels of isoprostanes or clinical symptoms determined from neuropsychological testing in the case of neuro inflammation.

2. The method of claim 1, wherein said weight ratio is between about 5:1 and about 100:1.

3. The method of claim 2, wherein said weight ratio is between about 10:1 and about 50:1.

4. The method of claim 1, wherein said administering comprises a method selected from the group consisting of oral delivery, intramuscular injection, intravenous injection, transdermal delivery, and transmucosal delivery.

5. The method of claim 4, wherein said administering comprises oral delivery.

6. The method of claim 1, wherein said administering further comprises administering a second disease treatment agent.

7. The method of claim 6, wherein said administering of the second treatment agent is before or after administration of the first treatment agent.

8. The method of claim 6, wherein said administering of a second treatment agent is coincident with administering the first treatment agent.

9. The method of claim 6, wherein the second treatment agent comprises one or more of the components selected from the group consisting of glucosamine sulfate, chondroitin sulfate, sea cucumber extract, hydrolyzed shark cartilage, collagen II, and methylsulfonylmethane.

10. The method of claim 1, wherein the agent is administered at a dosage of between about 0.3 mg/kg and 1 mg/kg per day.

11. The method of claim 10, wherein the agent is administered at a dosage of about 0.6 mg/kg per day.

12. The method of claim 1, wherein said subject is a human.

13. The method of claim 1, wherein said agent is dried to provide a powder extract.

14. The method of claim 1, wherein said agent is in the form of a tablet, capsule, or pill.

15. The method of claim 1, wherein said agent is in the form of a liquid or liquid drops.

16. A method of treating an inflammatory condition in a subject in need of such treatment, comprising administering to said subject a dosage amount corresponding to between about 0.1 mg/kg body weight and 2000 mg/kg body weight daily of substantially purified hydroxytyrosol or a substantially purified mixture of hydroxytyrosol and oleuropein, wherein said inflammatory condition is in response to a condition selected from the group consisting of: delayed type hypersensitivity reaction, psoriasis, an autoimmune disease, organ transplant, pain, fever, and tissue graft rejection.

* * * * *